United States Patent
Zeijlemaker et al.

(10) Patent No.: US 7,050,855 B2
(45) Date of Patent: May 23, 2006

(54) MEDICAL IMPLANTABLE SYSTEM FOR REDUCING MAGNETIC RESONANCE EFFECTS

(75) Inventors: Volkert A. Zeijlemaker, Landgraaf (NL); Ron Kalin, New Hope, MN (US); Gregory A. Hrdlicka, Plymouth, MN (US); Yong Kyun Cho, Maple Grove, MN (US); James D. Reinke, Maple Grove, MN (US); Laurie D. Foerster, Mound, MN (US)

(73) Assignee: Medtronic, Inc., Minneapolis, MN (US)

( * ) Notice: Subject to any disclaimer, the term of this patent is extended or adjusted under 35 U.S.C. 154(b) by 128 days.

(21) Appl. No.: 10/059,589

(22) Filed: Jan. 29, 2002

(65) Prior Publication Data

US 2003/0140931 A1 Jul. 31, 2003

(51) Int. Cl.
 *A61N 1/37* (2006.01)
(52) U.S. Cl. ..................................................... 607/27
(58) Field of Classification Search ................. 607/11, 607/27–29, 30–32, 57, 60; 324/260, 207.13, 324/207.2, 207.21
See application file for complete search history.

(56) References Cited

U.S. PATENT DOCUMENTS

| | | | |
|---|---|---|---|
| 4,091,818 A | 5/1978 | Brownlee et al. | |
| 4,541,431 A * | 9/1985 | Ibrahim et al. | 607/30 |
| 4,611,127 A * | 9/1986 | Ibrahim et al. | 307/116 |
| 5,217,010 A | 6/1993 | Tsitlik et al. | 128/419 PG |
| 5,292,342 A * | 3/1994 | Nelson et al. | 607/30 |
| 5,529,578 A | 6/1996 | Struble | 607/29 |
| 5,545,187 A * | 8/1996 | Bergstrom et al. | 607/32 |
| 5,562,714 A * | 10/1996 | Grevious | 607/32 |
| 5,694,952 A * | 12/1997 | Lidman et al. | 128/899 |
| 5,697,958 A | 12/1997 | Paul et al. | 607/31 |
| 5,764,052 A * | 6/1998 | Renger | 324/258 |
| 5,865,177 A * | 2/1999 | Segawa | 600/410 |
| 6,100,680 A * | 8/2000 | Vig et al. | 324/207.2 |
| 6,101,417 A * | 8/2000 | Vogel et al. | 607/30 |
| 6,161,046 A * | 12/2000 | Maniglia et al. | 607/57 |
| 6,188,926 B1 | 2/2001 | Vock | 607/9 |
| 6,198,972 B1 | 3/2001 | Hartlaub et al. | 607/63 |
| 6,209,764 B1 | 4/2001 | Hartlaub et al. | |
| 6,473,652 B1 * | 10/2002 | Sarwal et al. | 607/62 |
| 6,522,920 B1 * | 2/2003 | Silvian et al. | 607/2 |
| 6,625,493 B1 * | 9/2003 | Kroll et al. | 607/17 |
| 6,925,328 B1 * | 8/2005 | Foster et al. | 607/9 |
| 2002/0038135 A1 | 3/2002 | Connelly et al. | |
| 2002/0116028 A1 | 8/2002 | Greatbatch et al. | |
| 2002/0116029 A1 | 8/2002 | Miller et al. | |
| 2002/0116034 A1 | 8/2002 | Miller et al. | |
| 2002/0128689 A1 | 9/2002 | Connelly et al. | |

(Continued)

FOREIGN PATENT DOCUMENTS

FR 2805999 A1 6/2003

(Continued)

*Primary Examiner*—Jeffrey R. Jastrzab
(74) *Attorney, Agent, or Firm*—Daniel G. Chapik; Girma Wolde-Michael (57) ABSTRACT

Apparatus and methods are disclosed for reducing the potentially harmful effects of electromagnetic waves on an implantable medical device. In one embodiment of the present invention, an implantable medical system comprising a dual threshold magnetic sensor capable of detecting an elevated magnetic field is disclosed. The sensor can comprise a solid-state sensor capable of detecting a static magnetic field in excess of about 1500 Gauss. The magnetic sensor can be operatively coupled to electronics that are capable of altering the operation of the system upon detection of an elevated magnetic field by the magnetic sensor.

21 Claims, 7 Drawing Sheets

U.S. PATENT DOCUMENTS

| | | |
|---|---|---|
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/1038102 | 9/2002 | Weiner et al. |
| 2002/0143258 A1 | 10/2002 | Weiner et al. |
| 2002/0147470 A1 | 10/2002 | Weiner et al. |

FOREIGN PATENT DOCUMENTS

| | | |
|---|---|---|
| WO | WO 96/41203 | 12/1996 |

\* cited by examiner

SPECTRUM OF ELECTROMAGNETIC RADIATION

| REGION | WAVELENGTH (ANGSTROMS) | WAVELENGTH (CENTIMETERS) | FREQUENCY (Hz) | ENERGY (eV) |
|---|---|---|---|---|
| RADIO | $>10^9$ | $>10$ | $<3 \times 10^9$ | $<10^{-5}$ |
| MICROWAVE | $10^9 - 10^6$ | $10 - 0.01$ | $3 \times 10^9 - 3 \times 10^{12}$ | $10^{-5} - 0.01$ |
| INFRARED | $10^6 - 7000$ | $0.01 - 7 \times 10^{-5}$ | $3 \times 10^{12} - 4.3 \times 10^{14}$ | $0.01 - 2$ |
| VISIBLE | $7000 - 4000$ | $7 \times 10^{-5} - 4 \times 10^{-5}$ | $4.3 \times 10^{14} - 7.5 \times 10^{14}$ | $2 - 3$ |
| ULTRAVIOLET | $4000 - 10$ | $4 \times 10^{-5} - 10^{-7}$ | $7.5 \times 10^{14} - 3 \times 10^{17}$ | $3 - 10^3$ |
| X-RAYS | $10 - 0.1$ | $10^{-7} - 10^{-9}$ | $3 \times 10^{17} - 3 \times 10^{19}$ | $10^3 - 10^5$ |
| GAMMA RAYS | $<0.1$ | $<10^{-9}$ | $>3 \times 10^{19}$ | $>10^5$ |

*The notation "eV" stands for electron-volts, a common unit of energy measure in atomic physics.*

FIG. 7

MEDICAL IMPLANTABLE SYSTEM FOR REDUCING MAGNETIC RESONANCE EFFECTS

FIELD OF THE INVENTION

This invention relates generally to a method and apparatus for electrically stimulating a heart, and, more particularly, to a method and apparatus for reducing the effects of an electro-magnetic field on the operation and safety of implantable medical devices.

DESCRIPTION OF THE RELATED ART

Since the introduction of the first implantable pacemakers in the 1960s, there have been considerable advancements in both the fields of electronics and medicine, such that there is presently a wide assortment of commercially available body-implantable electronic medical devices. The class of implantable medical devices now includes therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks. The therapeutic benefits of such devices have been well proven.

Modern electrical therapeutic and diagnostic devices for the heart require a reliable electrical connection between the device and a region of the heart. Typically, an electrical contact, commonly referred to as a "lead," is used for the desired electrical connection. One type of commonly used implantable lead is a transvenous lead. Transvenous leads are generally positioned through the venous system to attach and/or electrically connect at their distal end via a tip electrode to the heart. At their proximal end, they are typically connected to the electrical therapeutic and/or diagnostic device, which may be implanted. Such leads normally take the form of a long, flexible, insulated conductor. Among the many advantages of transvenous leads is that they permit an electrical contact with the heart without physically exposing the heart itself, i.e., major thoracic surgery is not required.

Other advancements in medical technology have led to improved imaging technologies, for example magnetic resonance imaging (MRI). MRI generates cross-sectional images of a human body by using nuclear magnetic resonance (NMR). The MRI process begins with positioning the body to be imaged in a strong, uniform magnetic field, which polarizes the nuclear magnetic moments of protons within hydrogen molecules in the body by forcing their spins into one of two possible orientations. Then an appropriately polarized radio-frequency field, applied at resonant frequency, forces spin transitions between these orientations. The spin transitions create a signal, an NMR phenomenon, which can be detected by a receiving coil.

Further, shortwave diathermy, microwave diathermy, ultrasound diathermy, and the like have been shown to provide therapeutic benefits to patients, such as to relieve pain, stiffness, and muscle spasms; to reduce joint contractures; to reduce swelling and pain after surgery; to promote wound healing; and the like. Generally, energy (e.g., shortwave energy, microwave energy, ultrasound energy, or the like) is directed into a localized area of the patient's body.

Traditionally, the use of the above-described therapies have been discouraged for patients having such implanted medical devices, as the environment produced by the MRI or diathermy apparatuses is generally considered hostile to implantable medical devices. The energy fields generated during the MRI or diathermy processes, may induce an electrical current in leads that can be dissipated within tissue adjacent lead electrodes. This may cause tissue damage if the current densities attain unacceptably high levels. Additionally, a sudden burst of radio-frequency energy can deliver a current pulse that may induce a tachycardia or fibrillation. Improperly sensed signals may also result in inappropriately delivered therapy, include inappropriate pacing rates and/or unnecessarily delivered shocks.

What is needed, therefore is an improved method and apparatus for reducing the detrimental effects that are possible when a patient with an implantable electrical lead is subjected to an electromagnetic field.

SUMMARY OF THE INVENTION

In one aspect of the present invention, an implantable medical system comprising a magnetic sensor capable of detecting a magnetic field having a magnetic field strength within a predetermined range. In one exemplary embodiment, the sensor can comprise a solid-state dual threshold magnetic field sensor capable of detecting a static magnetic field in excess of a predetermined level, which may be about 1500 Gauss. The system further includes at least one circuit, the operations of which are controlled by magnetic field strength measurements obtained by the magnetic field sensor. The at least one circuit may include additional physiological sensors, communications circuits, switches, and leads, for example. Any one or more of these may be disabled, enabled, or otherwise controlled based on the magnetic field measurements. In one embodiment, current and/or voltage signals in the leads may be limited based on elevated magnetic field strength measurements. In an embodiment wherein the system includes one or more leads, ones of the leads may be coupled to electronic filters to alter transmission of signals having a predetermined frequency range.

In another embodiment of the invention, an implantable medical system comprises electronics capable of monitoring and controlling the functioning of the implantable medical system. At least one electrical lead may be operatively coupled to the electronics. The electronics controls current flow within the electrical lead when the system detects a magnetic field having a field strength above a predetermined level.

Still another embodiment of the invention includes an implantable medical system having electronics to monitoring and control the operation of the implantable medical system, and at least one electrical lead operatively coupled to the electronics. At least one filter is operatively coupled to the at least one electrical lead capable of attenuating a signal within the at least one electrical lead.

A method is also provided for operating an implantable medical system. The method includes measuring the field strength of a magnetic field, and controlling the operation of the implantable medical system based upon those measurements. Other aspects and embodiments of the invention will become apparent from the following description and the accompanying drawings.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
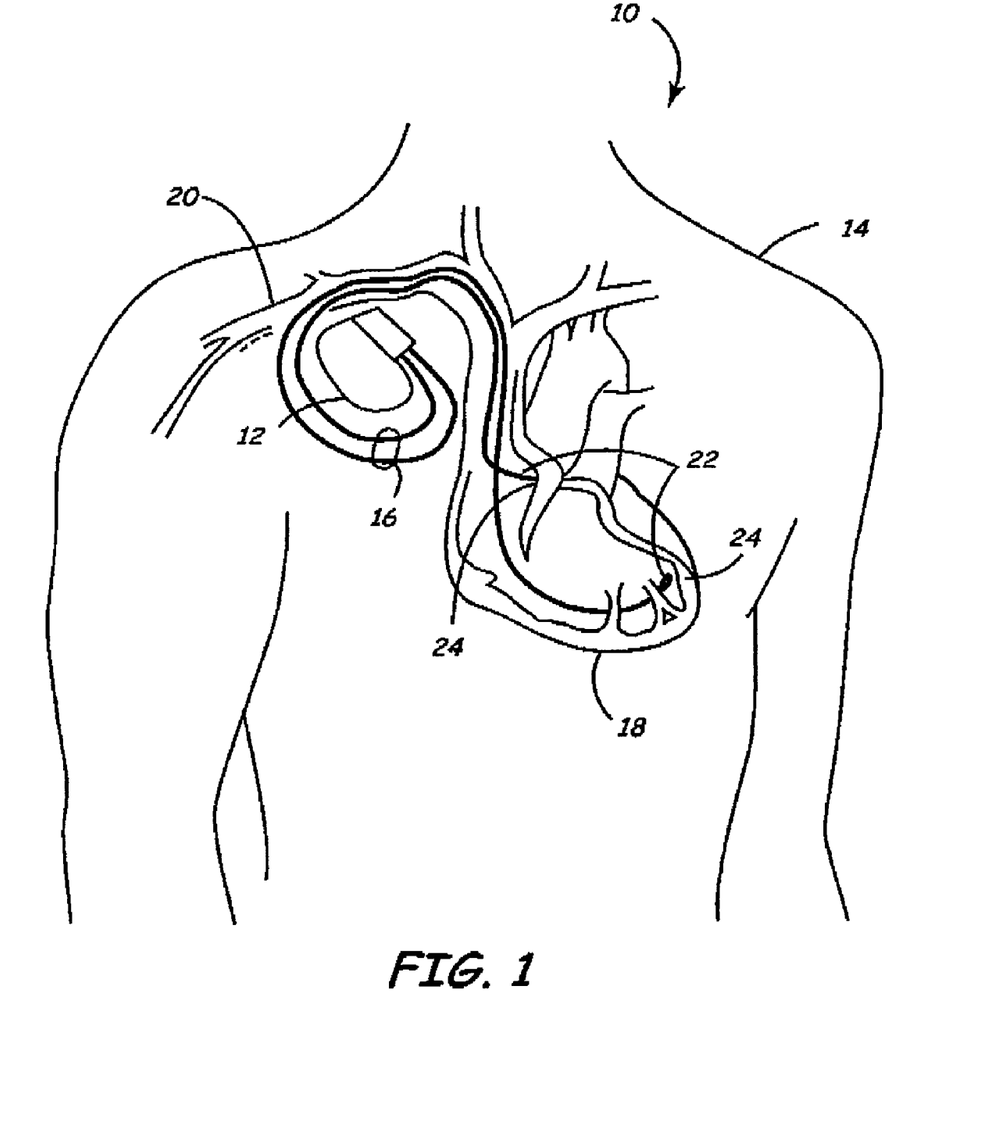
FIG. 1 schematically illustrates a prior art implanted medical device within a human body.

FIG. 1 illustrates a prior art implantable medical device (IMD) system 10, which includes an implantable electronic device 12, such as a pacemaker, defibrillator, or the like, that has been implanted in a patient's body 14. One or more pacemaker leads, collectively identified with reference numeral 16, are electrically coupled to the pacemaker 12 in a conventional manner and extend into the patient's heart 18 via a vein 20.

Located generally near the distal end 22 of the leads 16 are one or more exposed conductive electrodes 24 that are attached to the heart 18 tissue, sensing cardiac activity, delivering electrical pacing stimuli to the heart 18, or providing a stimulating voltage to defibrillate the heart 18. The contact area between the electrodes 24 and the heart 18 tissue is very small as compared, for example, to the contact area between the device 12 and the body 14.

Figure 2:
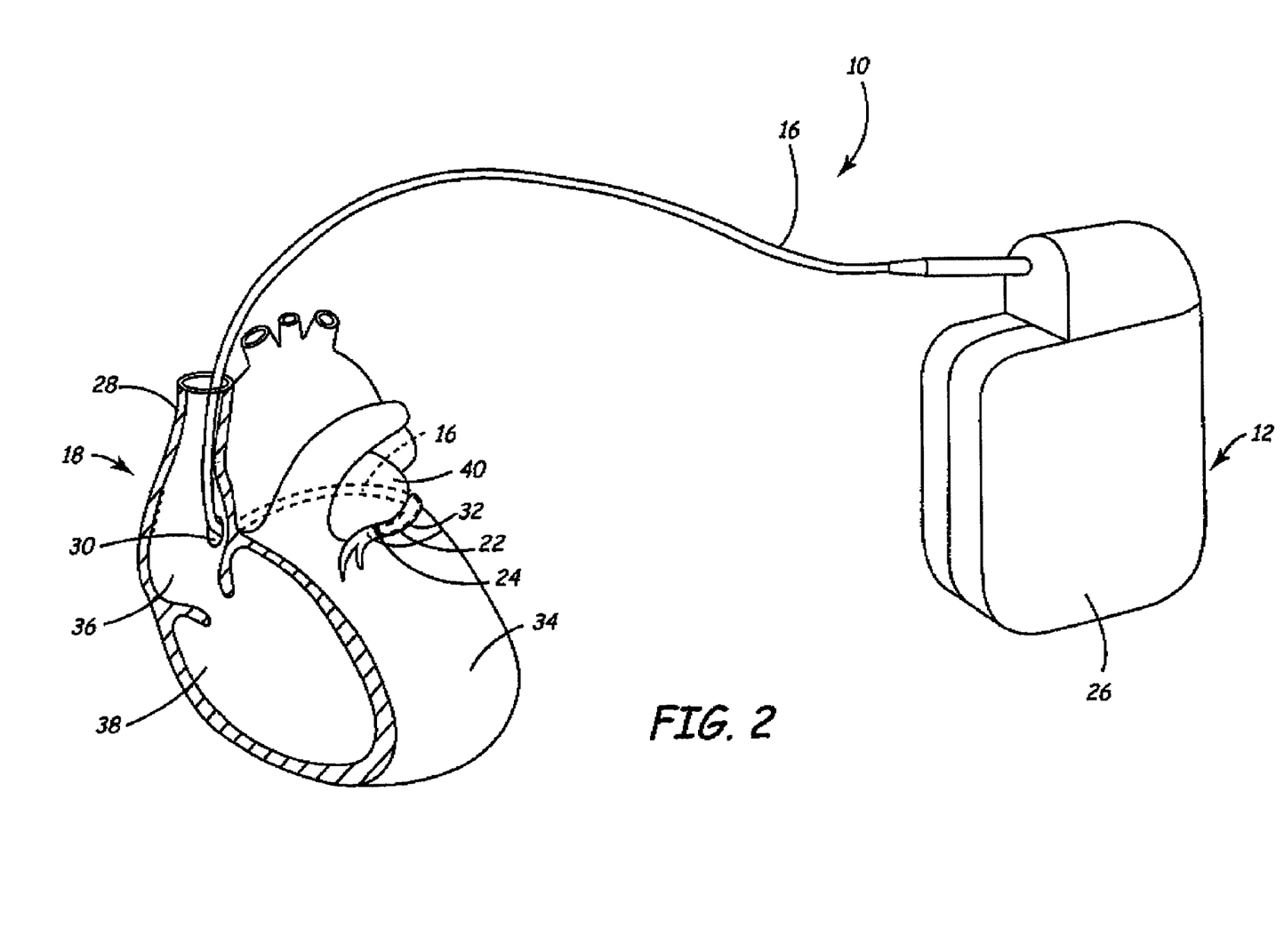
FIG. 2 schematically illustrates a prior art embodiment of an implanted medical device with an endovenous epicardial lead positioned adjacent the left ventricle of a heart.

FIG. 2 illustrates a prior art implantable medical device (IMD) system 10, which includes an implantable electronic device 12, such as a pacemaker or defibrillator. The device 12 is housed within a hermetically sealed, biologically inert outer canister or housing 26, which may itself be conductive. One or more leads 16 are electrically coupled to the device 12 and extend to a point adjacent the patient's heart 18 via a vein, typically the superior vena cava vein 28. This embodiment illustrates a lead 16 proceeding from the right atrium 36, through the coronary sinus 30 and its distal end 22 positioned within a cardiac vein 32 that is adjacent to the left ventricle 34 of the heart 18. An electrode 24, for example, a ring electrode, is placed in contact with the cardiac vein 32 to provide the necessary electrical proximity between the device 12 and the heart 18. Leads can also be placed within the right atrium 36 and the right ventricle 38 of the heart 18. This illustration shows the relatively small contact area between the electrode 24 and the tissue of the vein 32.

Figure 3:
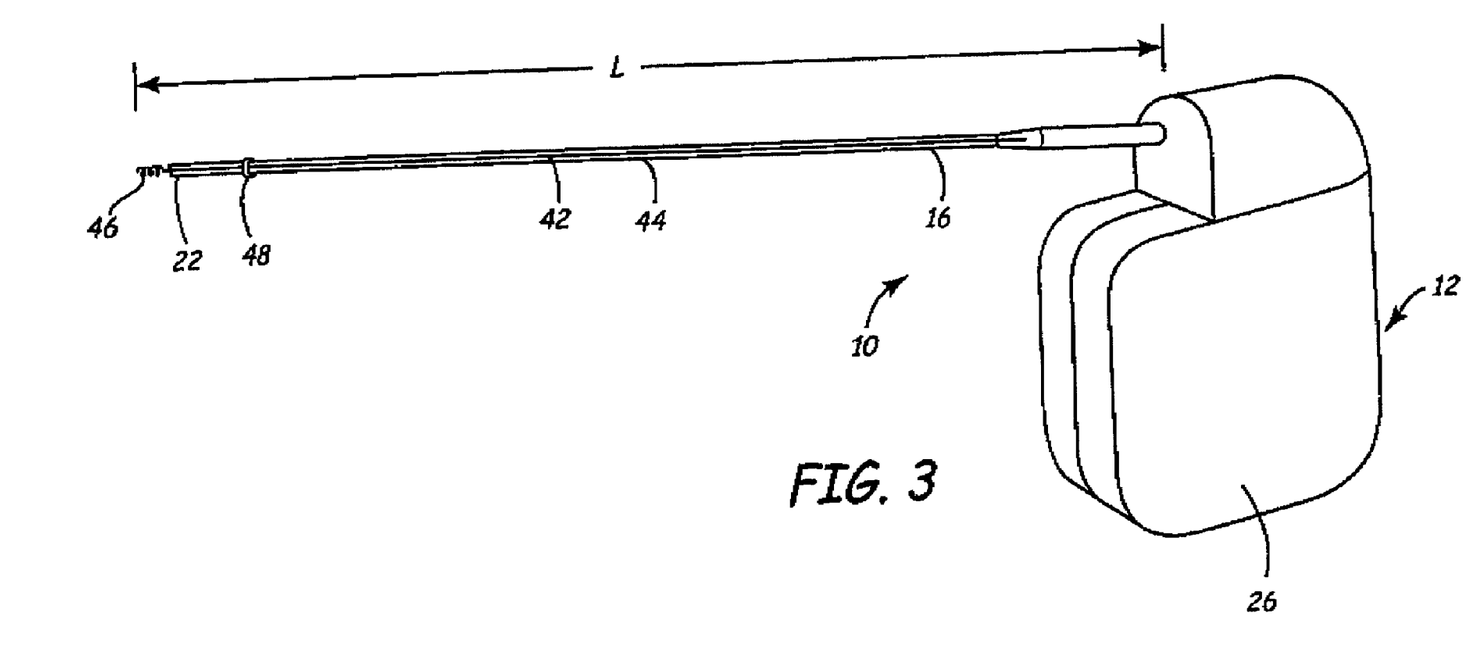
FIG. 3 schematically illustrates a prior art embodiment of an implantable medical device with a tip electrode located at the distal end of the lead.

FIG. 3 schematically illustrates an embodiment of an implantable medical system 10 having an electrical lead 16 having a length L. The electrical lead 16 is shown as a cross section to show the electrode conductor 42 surrounded by an insulator 44. A tip electrode 46 is shown at distal end 22, and a ring electrode 48 is shown proximal tip electrode. More or fewer electrodes may be provided by the lead. One embodiment of a tip electrode 46 comprises a helical coil that can be affixed directly to heart tissue and is particularly useful in attaching the lead 16 within an atrium or ventricle chamber wall of a heart 18. The ring electrode 48 may include a protrusion such as a ridge having a larger diameter than the remainder of the lead 16, as may be useful when a lead is positioned within a vein, such as the cardiac vein 32 shown in FIG. 2. The lead 16 can comprise more than one electrode conductors such as electrode conductor 42. In a multi-polar embodiment such as shown in FIG. 3, separate electrode conductors are generally coupled to tip electrode 46 and ring electrode 48, respectively.

Figure 4:
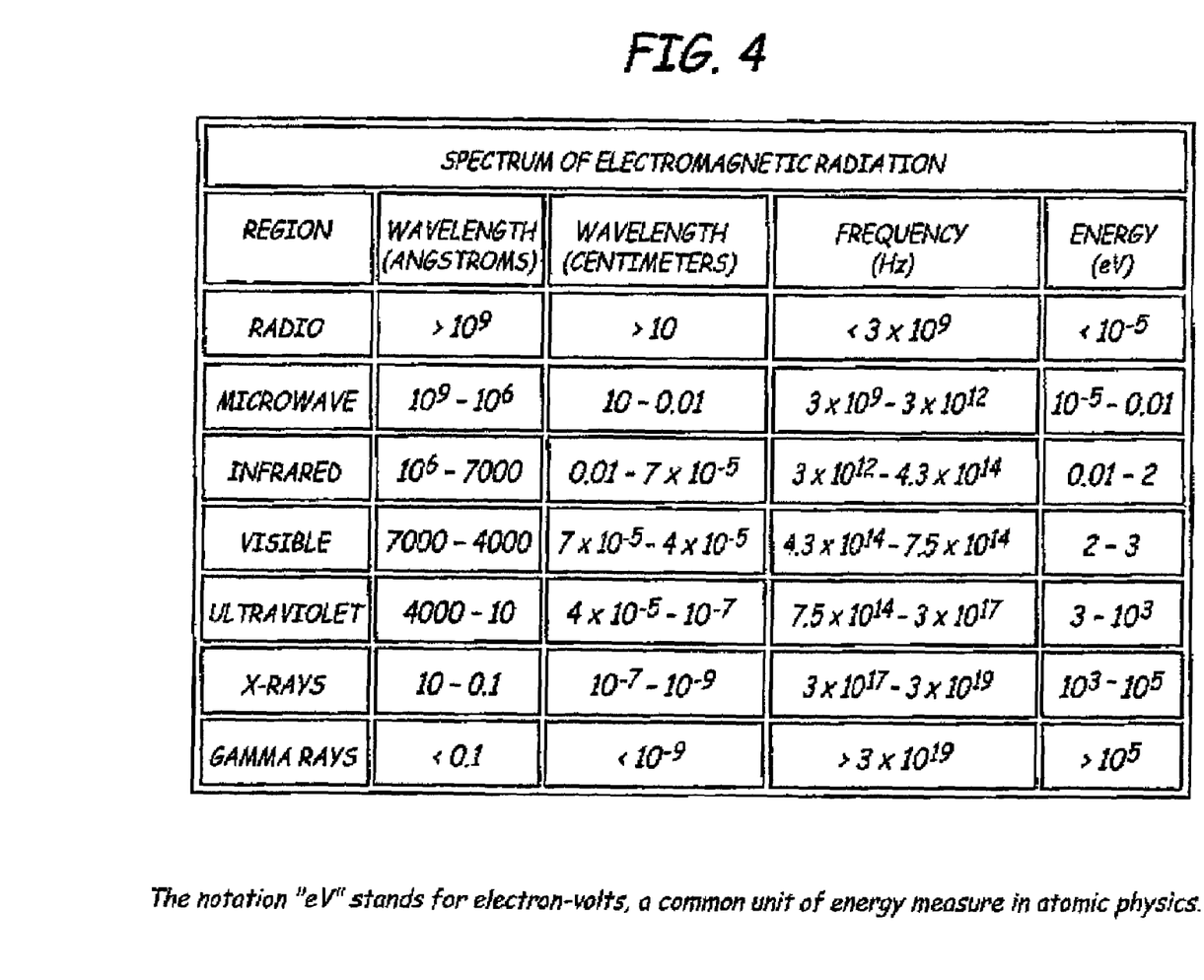
FIG. 4 is a table showing various named regions of the electromagnetic spectrum along with their respective wavelength, frequency and energy ranges.

FIG. 4 is a table showing various named regions of the electromagnetic spectrum along with their respective wavelength, frequency and energy ranges. As the frequency increases, the amount of energy that is transmitted increases as well.

Electromagnetic fields may be described using a unit of magnetic flux density known as a "Tesla." Another unit of measure commonly used is the "gauss", where 1 Tesla equals 10,000 gauss. The magnets in use today in MRI systems generate magnetic fields having a flux density in the 0.5–2.0 Tesla range, or 5,000–20,000 gauss.

An MRI system of 1 Tesla will operate at a frequency of approximately 42 MHz or 42×10E6 hertz. This is within the radio region of the electromagnetic radiation spectrum and is commonly referred to as radio-frequency (RF) energy. In the search for better diagnostic capabilities, MRI systems utilizing even stronger magnets capable of generating increasing amounts of RF energy are being developed. The greater the level of RF energy transmitted, the greater the risk of injuring a patient by inducing electrical currents within an implanted lead as is described below.

Figure 5:
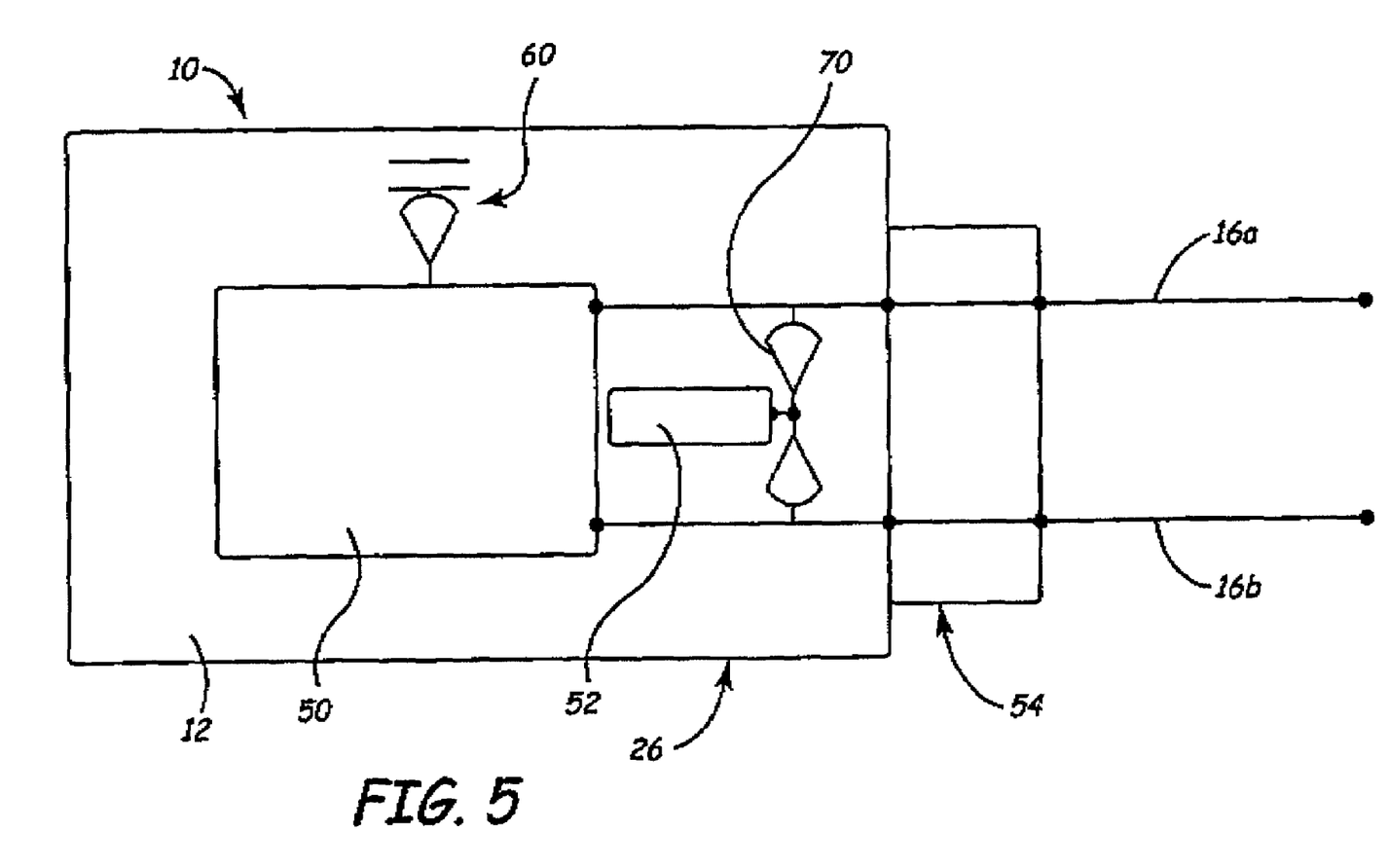
FIG. 5 is a generalized drawing of an embodiment of the present invention.

FIG. 5 is a generalized drawing of an embodiment of the present invention comprising an implantable system 10 having an electronic device 12 enclosed within a housing 26. Electronics 50 and a power supply 52 are contained within the device 12 and are operatively coupled to a pair of electrical unipolar leads 16a and 16b by a connector 54. It will be understood that the system may be coupled to any number of leads as needed, and multipolar leads may be used in addition to, or instead of, the unipolar leads. The electronics 50 are capable of monitoring and controlling the operation of the implantable medical system 10, and may comprise digital, analog, firmware and/or other type electrical components as is known in the art.

The system of FIG. 5 includes a magnetic sensor 60 operatively coupled to the electronics 50. The sensor 60 may be used to detect a magnetic field level that is above the normal background magnetic field of the earth, may detect a magnetic field level that is above a predetermined level, or may detect a change in the magnetic field surrounding the environment in which the implantable system 10 is located. The magnetic sensor 60 may be capable of detecting multi-level magnetic field strengths and/or may be capable of discriminating between different magnetic field ranges.

In one embodiment of the invention, the sensor 60 may comprise a solid-state dual threshold magnetic field sensor that is based on the Hall effect, or may comprise any other type of magnetic field sensor known in the art. In the case of a dual-threshold magnetic field sensor, multiple magnetic field levels are provided to allow the device to alter its mode of operation based on these detected magnetic field levels. The sensor 60 can provide signals to the electronics 50 that are used to alter system operations when an elevated magnetic field is detected. For example, electronics 50 can alter system operations to reduce or minimize the current flow and/or the voltage levels within leads 16a and/or 16b when the static magnetic field is greater than a pre-determined level, for example, 1500 Gauss or 0.15 Tesla.

Normal system operation may be resumed after the sensed magnetic field strength is reduced to a predetermined level, and/or upon resetting or reprogramming the device 12. The predetermined level may be the total elimination of any elevated magnetic field above the normal background magnetic field of the earth, or could be at a predetermined elevated level. For example, the system 10 may be set to resume normal system operations upon a sensing of the static magnetic field of 1500 Gauss or less. The system 10 may resume normal system operation upon a resetting or reprogramming of the device 12, for example, by an electrical or magnetic signal sent by an external device to the implanted device 12. This may be accomplished by a physical manipulation of the device 12, or via a communication transmission between the system and an external device such as a programmer.

In one embodiment, filters 70 may provide a low impedance path from the two leads to a terminal of the power supply 52. For example, filters 70 may comprise one or more low-pass filters adapted to attenuate currents when leads 16a and 16b are within an electromagnetic field. This reduces the magnitude of induced current that can pass through the leads and into the patient. Such filters may include any of the embodiments described in U.S. Pat. No. 5,217,010 incorporated herein by reference. Filters 70 are shown as being positioned within the device 12, however the filters may also be positioned elsewhere, for example, in the connector 54 or lead 16.

Figure 6:
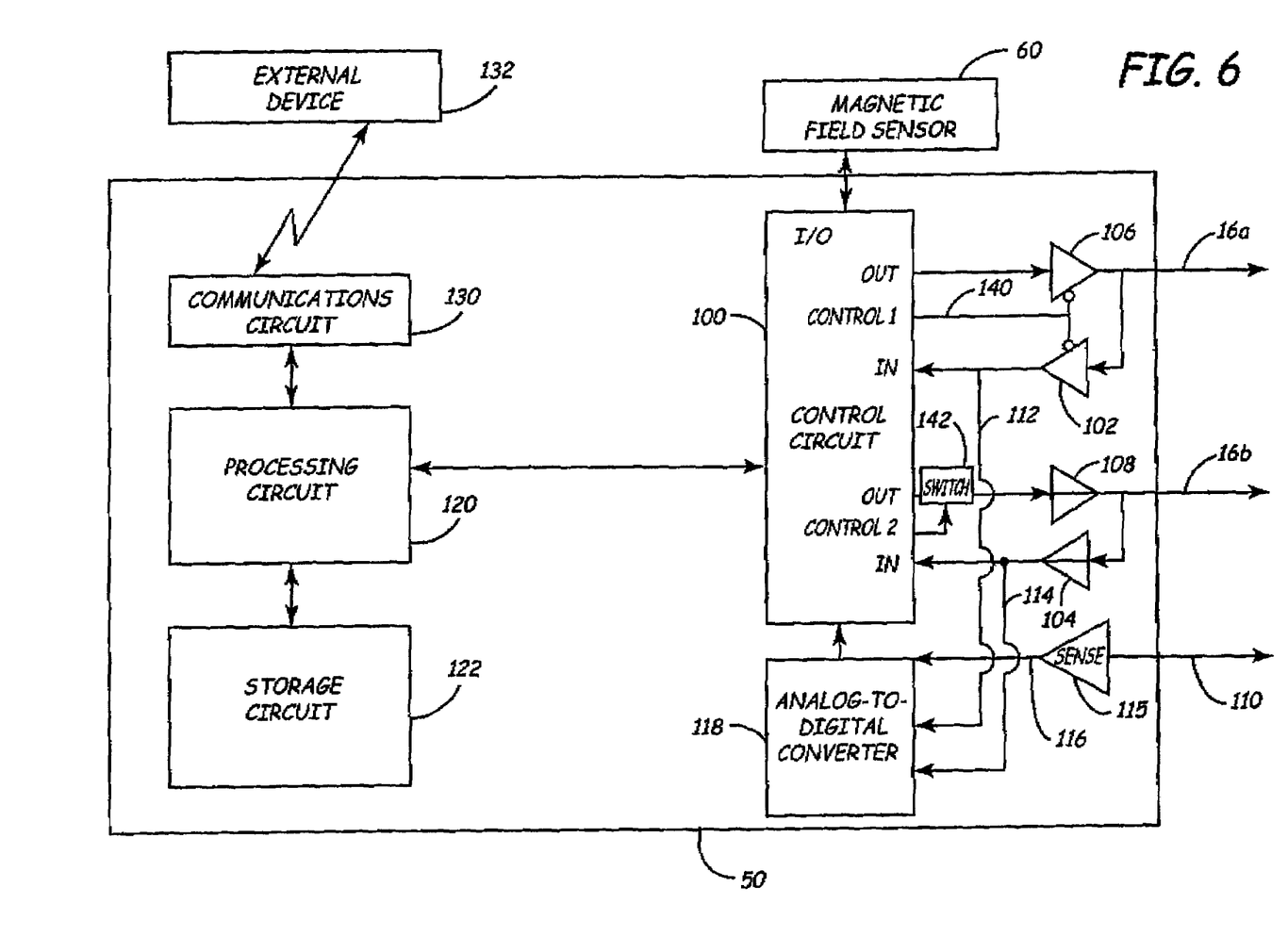
FIG. 6 is a block diagram of one embodiment of circuitry that may be included within the system shown in FIG. 4.

FIG. 6 is a block diagram of one embodiment of circuitry that may be included in electronics 50 of FIG. 4. The circuitry includes a control circuit 100, which may be a timer/counter circuit or another circuit for controlling timing and/or voltage levels associated with electrical stimulation provided on leads 16a and 16b. As noted above, the electrical stimulation may include pacing pulses, high-voltage shocks, electrical stimulation pulses provided to muscle or nerve tissue, or any other type of stimulation required per a given therapy regimen. In the case of high-voltage therapy as associated with cardioversion/defibrillation systems, control circuit 100 includes a high-voltage output circuit that may comprise high-voltage capacitors and charging circuits as is known in the art.

Control circuit 100 is coupled to leads 16a and 16b via input amplifiers 102 and 104, respectively. In a similar manner, these leads may be coupled to control circuit 100 via output amplifiers 106 and 108, respectively, as is known in the art. In one embodiment, input signals from leads 16a and 16b may be provided on lines 112 and 114 to an analog-to-digital converter 118 to be converted to digital format before being transferred to control circuit 100.

Control circuit 100 may be further coupled to one or more additional sensors to sense biological signals on signal lines 110 via amplifiers such as sense amplifier 115. Such sensors may include pressure, temperature, acceleration, impedance, or other type of sensors. Control circuit 100 is also coupled to magnetic field sensor 60, allowing the control circuit to read magnetic field levels measured by the magnetic field sensor.

In one embodiment, the magnetic field sensor may be of a type that provides a digital or analog signal indicate of an actual field level. This signal can be used by the system in any of the ways discussed below to control system operation. In another embodiment, the magnetic field sensor can be adapted to send a signal when a magnetic field strength is measured to be above or below one or more levels.

Electronics 50 may further contain a processing circuit 120, which may include any combination of integrated and discrete digital and/or analog components. In one embodiment, processing circuit 120 may be a microprocessor. Processing circuit 120 may read magnetic field levels from magnetic field sensor 60, as well as other sensed signals, via the control circuit 100. As discussed above, the magnetic field sensor may have the capability to send signals to processing circuit 120 when a predetermined field strength is detected, thereby allowing for operation in an interrupt-driven mode rather than a polling mode.

Processing circuit is further coupled to storage circuit 122, which may be any combination of random access memory (RAM), read-only memory (ROM) and/or any other type of storage device. Storage circuit 122 may store the programmed instructions executed by processing circuit 120, and any operating parameters and/or other data needed by the system. Storage circuit may further store any of the sensed signals, including magnetic field levels, measured by the system. Processing circuit may also be coupled to a communication circuit 130 such as a telemetry circuit that is adapted to communicate with one or more external devices 132, which may include a programmer.

As noted above, device 50 may control any one or more of the desired functions of the system based on measurements obtained from magnetic field sensor 60. In one embodiment, a control line 140 or similar control signals may be used to disable amplifiers such as amplifiers 106 and 102 when a predetermined magnetic field strength is detected. This may be performed to prevent electrical stimulation such as pacing pulses from being delivered to a patient during this time. Additionally, sensing may be discontinued until the magnetic field strength returns to a predetermined level, since the noise introduced by the magnetic field may make sensing inaccurate. In another embodiment, electrical stimulation may be continued in an asynchronous manner while only sensing is discontinued.

According to one embodiment, the detection of a magnetic field having a predetermined strength may be used to open or close switches such as switch 142. Switches of this manner could be used to disconnect one or more predetermined signal lines so that pacing, sensing, and/or other operations are discontinued during the time a patient is undergoing an MRI procedure. In one embodiment, switches could include one or more field effect transistors (FETs). In another embodiment, one or more of the switches could be implemented using Micro-Electrical-Mechanical systems (MEMs) technology, as is disclosed in U.S. patent application Ser. No. 10/004,025 filed Nov. 1, 2001 incorporated herein by reference in its entirety. Any other type of switch known in the art and suitable for use in an implantable medical device may be adapted for use in the system.

In another embodiment of the invention, communications circuit 130 may be disabled so that no communication transmissions occur during the presence of a magnetic field having a predetermined strength. As an alternative, only predetermined communication transmissions may be disabled, such as uplink transmission. This will prevent the possibility of erroneous data being transmitted because of the noise generated by the magnetic field. In a similar manner, sensing using any biological sensors may be prevented by disabling sense amplifiers such as sense amplifier 115 so that noise does not result in erroneous readings. Any other type of function of the system may be selectively disabled, enabled, or altered based on sensing a predetermined magnetic field strength level, and the foregoing are to be considered exemplary in nature only. As mentioned previously, this may involve sensing a magnetic field having a field strength above a predetermined level, or within a predetermined range. Additionally, one or more magnetic field measurements may be averaged or otherwise processed to gain a more accurate measurement for use in controlling the system.

Figure 7:
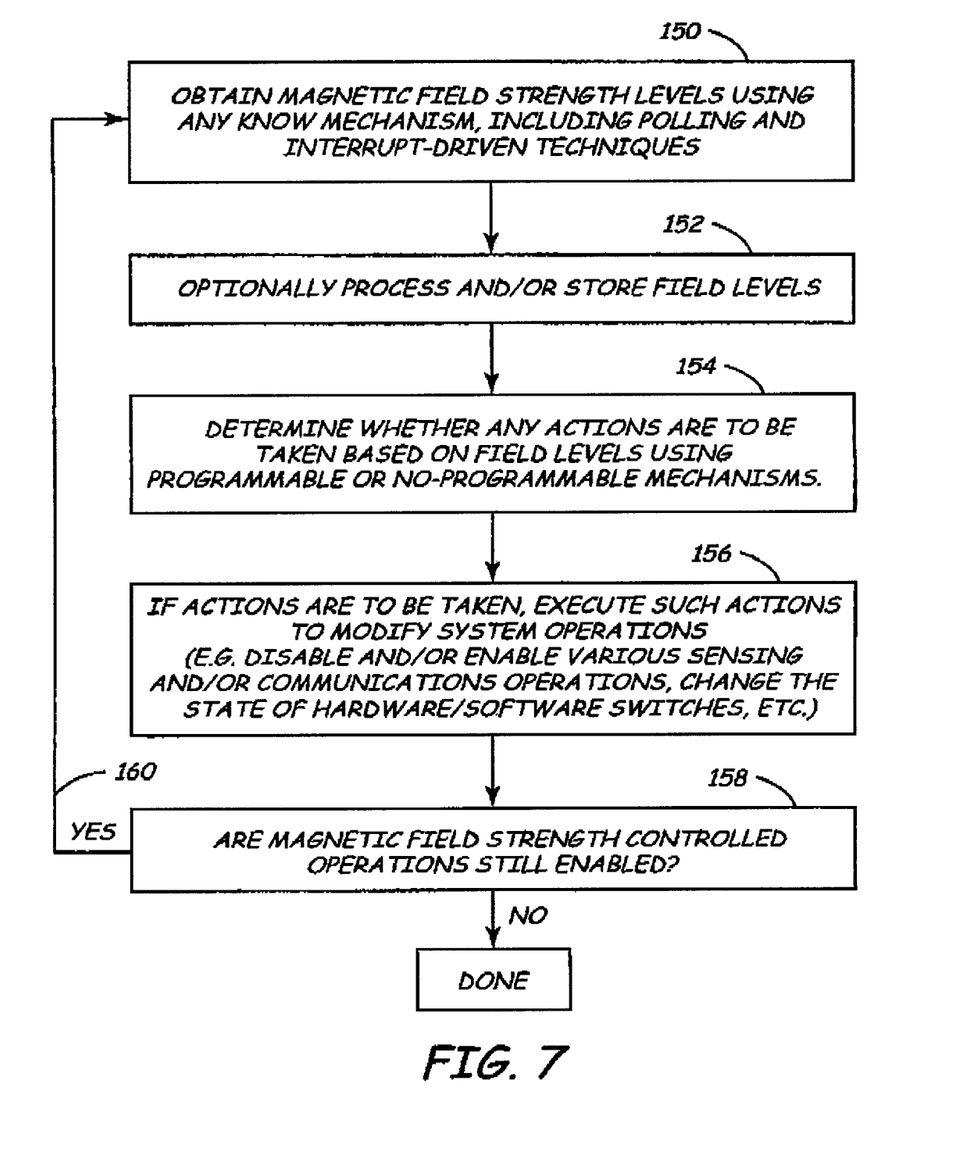
FIG. 7 is a flow diagram illustrating the operation of an embodiment of the system according to the current invention.

FIG. 7 is a flow diagram illustrating an exemplary operation of the inventive system. First, magnetic field strength measurements are obtained for use in controlling the system (150). These measurements may be obtained either continuously or at predetermined times. In one embodiment, a magnetic field sensor may be adapted to provide the processing circuit 120 with one or more signals when the measured magnetic field strength has reached one or more predetermined levels. In this embodiment, the processing circuit may operate in an interrupt-driven mode, such that actions are taken only when the processing circuit receives a predetermined interrupt signal. Alternatively, a magnetic field sensor may be utilized that provides analog or digital representations of measured signal levels. In this embodiment, processing circuit may operate in a polling mode to periodically read these representations. These measured signal levels may be processed and/or stored by processing circuit in any manner desired to obtain a final representation of the magnetic field strength (152).

After a representative of the magnetic field strength has been obtained by the system, a determination is made as to whether any action should be taken (154). In a system capable of detecting multiple field strength ranges, various actions may be defined for various field strength ranges. For example, if a magnetic field strength is detected that falls within a slightly elevated field strength range, a predetermined action may involve disabling a first set of sensors. If the magnetic field strength increases so that it falls within another predetermined range, the associated action may involve disabling another set of sensors. A further increase may involve disabling communications with an outside device, and so on. If desired, software and/or firmware flags may be set so that various software functions within the system are enabled or disabled based on the magnetic field strength measurements. In one embodiment, the magnetic field strength ranges and associated pre-defined actions may be software programmable using a lookup table, for example. In another embodiment, the desired actions may be hard-coded.

After the system had determined which, if any, action(s) should be performed based on a detected magnetic field strength level, these actions may be performed by the processor alone, or in conjunction with other control circuits within the system (156). As discussed above, this may involve enabling or disabling any of the hardware, software, firmware, and/or other logic functions within the system. For example, sensors and/or communication circuits may be enabled and/or disabled, and switches may be opened or closed to electrically couple or de-couple circuits from the system. In one instance, it may be desirable to de-couple one or more medical electrical leads from electronics 50 when a predetermined magnetic field strength is detected.

If desired, the system could include a master hardware and/or software switch that disables the use of magnetic field strength measurements in controlling system functions. (158). Otherwise, the operations shown in FIG. 7 may be continued (160).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below.

What is claimed is:

1. An implantable medical system, comprising;
    an operational control subsystem for controlling a therapy delivery component of the implantable medical system, wherein the therapy delivery component includes at least one therapy delivery lead;
    a magnetic sensor to measure a magnetic field surrounding the environment in which the system is located and provide a magnetic field strength value indicative of the magnitude of the magnetic field;
    at least one circuit coupled to the operational control subsystem and the magnetic sensor to receive the magnetic field strength value and compare the magnetic field strength value to a threshold value and output a control signal to the operational control system if the magnetic field strength value exceeds the threshold, wherein the threshold value is a predetermined value above which the environmental magnetic field is capable of adversely interfering with normal operation of the therapy delivery lead; and
    an adjustment component communicatively coupled with the operational control system, wherein the adjustment component controls a portion of the therapy delivery component if the operational control system receives the control signal.

2. The system of claim 1, wherein the magnetic sensor comprises a solid-state dual threshold sensor.

3. The system of claim 2, wherein the magnetic sensor is based on a Hall effect sensor.

4. The system of claim 1, wherein the magnetic sensor is capable of detecting a static magnetic field in excess of about 1500 Gauss.

5. The system of claim 1, wherein the threshold value is about 1500 Gauss.

6. The system of claim 1, wherein the at least one circuit includes at least one additional sensor, and operation of the at least one additional sensor is controlled based on magnetic field strength valued provided by the magnetic sensor.

7. The system of claim 1, wherein the at least one circuit includes a communication circuit, and operation of the communication circuit is controlled in part by the adjustment component if the operational control system receives the control signal.

8. The system of claim 1, wherein the adjustment component includes at least one switch, and a state of the switch is determined based on the presence or absence of the control signal.

9. The system of claim 1, wherein the adjustment component includes a circuit to reduce an electrical current flow within the therapy delivery lead if the operational control system receives the control signal.

10. The system of claim 1, wherein the at least one electrical lead is coupled to a filter controlled by the adjustment component.

11. The system of claim 10, wherein the filter includes a circuit to attenuate flow of current having a frequency within a predetermined frequency range.

12. An implantable medical system, comprising:
    means for operating a therapy delivery lead of the implantable medical system
    a magnetic sensor for measuring a magnetic field strength;
    comparison means for receiving a measured magnetic field strength value from the magnetic sensor and comparing the measured magnetic field strength value to a threshold value and generating a control signal to the means for operating if the measured magnetic field strength value exceeds the threshold value, wherein the threshold value is a predetermined value above which the magnetic field is capable of adversely interfering with normal operation of the therapy delivery lead; and
    means for modifying the operation of the therapy delivery lead if the comparison means generates the control signal.

13. The system of claim 12, wherein the means for modifying include a circuit capable of reducing electrical current flow within the therapy delivery lead if the comparison means generates the control signal.

14. The system of claim 13, wherein the means for modifying include a circuit to resume normal operation of the system when the measured magnetic field strength is less than the threshold.

15. A method of operating an implantable medical system, comprising:
    operating the implantable medical system in a normal mode of operation;
    measuring a magnetic field strength;
    comparing the measured magnetic field strength to a threshold value, wherein the threshold value is a predetermined value indicative of a magnetic field strength above which the magnetic field is capable of interfering with a therapy delivery lead of the implantable medical system; and
    altering an operation of a therapy delivery lead of the medical system if the measured field strength value exceeds the threshold.

16. The method of claim 15, wherein altering an operation includes limiting electrical current flow within the therapy delivery lead.

17. The method of claim 15, wherein the predetermined value is about 1500 Gauss.

18. The method of claim 15, and further comprising:
    terminating the alteration of the therapy delivery lead if the measured magnetic field strength falls below the threshold value.

19. The method of claim 15, wherein the system further includes a sensor, and altering an operation includes modifying use of the sensor within the system.

20. The method of claim 15, wherein the system includes a communication circuit, and altering an operation further includes modifying use of the communication circuit within the system.

21. The method of claim 15, wherein the system includes at least one switch, and altering an operation includes controlling a state of the switch based on the measured magnetic field strength.

* * * * *